United States Patent [19]

Truglio

[11] Patent Number: 5,433,741
[45] Date of Patent: Jul. 18, 1995

[54] THERMALLY-INTERACTIVE BACKBOARD

[76] Inventor: Francis G. Truglio, 12201 Wilderness Park Dr., Spotsylvania, Va. 22553

[21] Appl. No.: 136,005

[22] Filed: Oct. 14, 1993

[51] Int. Cl.⁶ ............................................. A61F 7/00
[52] U.S. Cl. ...................................... 607/104; 5/421; 607/112; 128/870
[58] Field of Search .............. 5/421, 422, 450, 451, 5/629, 628; 128/876, 872; 607/104–111, 112, 114; 165/46, 168

[56] References Cited

U.S. PATENT DOCUMENTS

| | | | |
|---|---|---|---|
| 1,970,200 | 9/1932 | Short | 607/104 |
| 4,884,304 | 12/1989 | Elkins | 5/421 |
| 5,016,620 | 5/1991 | Matthews | 128/870 |
| 5,184,612 | 2/1993 | Augustine | 607/104 |

Primary Examiner—Kyle L. Howell
Assistant Examiner—Robert L. Nasser, Jr.
Attorney, Agent, or Firm—Ostrolenk, Faber, Gerb & Soffen

[57] ABSTRACT

A backboard with internal ducts for circulation of heated and/or cooled liquid or gas for treating a post-traumatic-injury patient, specifically a patient with a severe back injury. The backboard provides three vital functions for the patient: (1) immobilization (2) maintaining body core temperature, and (3) reduction/prevention of inflammation and/or edema. The thermally-interactive unit is constructed of radiolucent materials for compatibility with x-ray equipment, and is compatible with sterilization requirements.

5 Claims, 6 Drawing Sheets

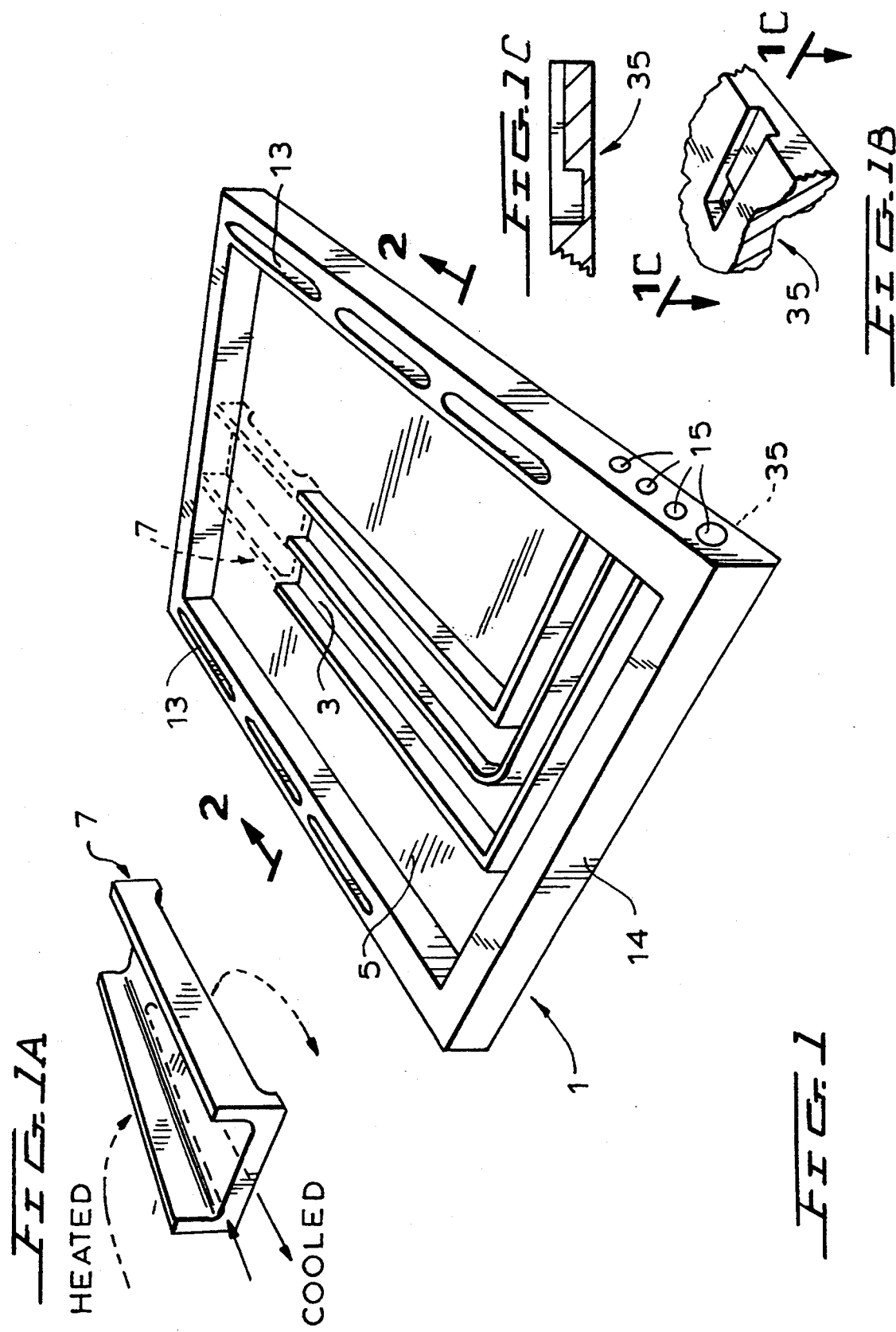

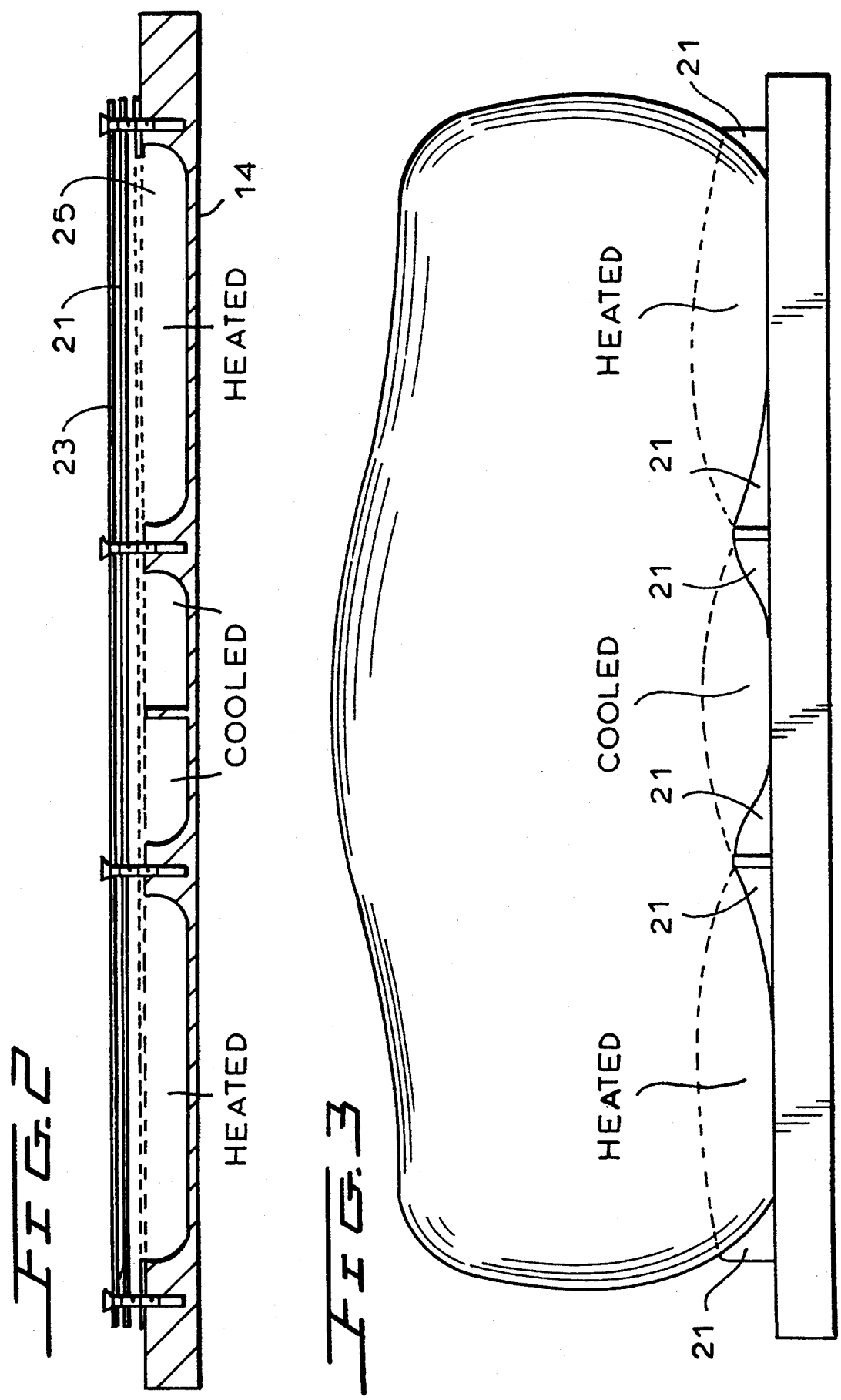

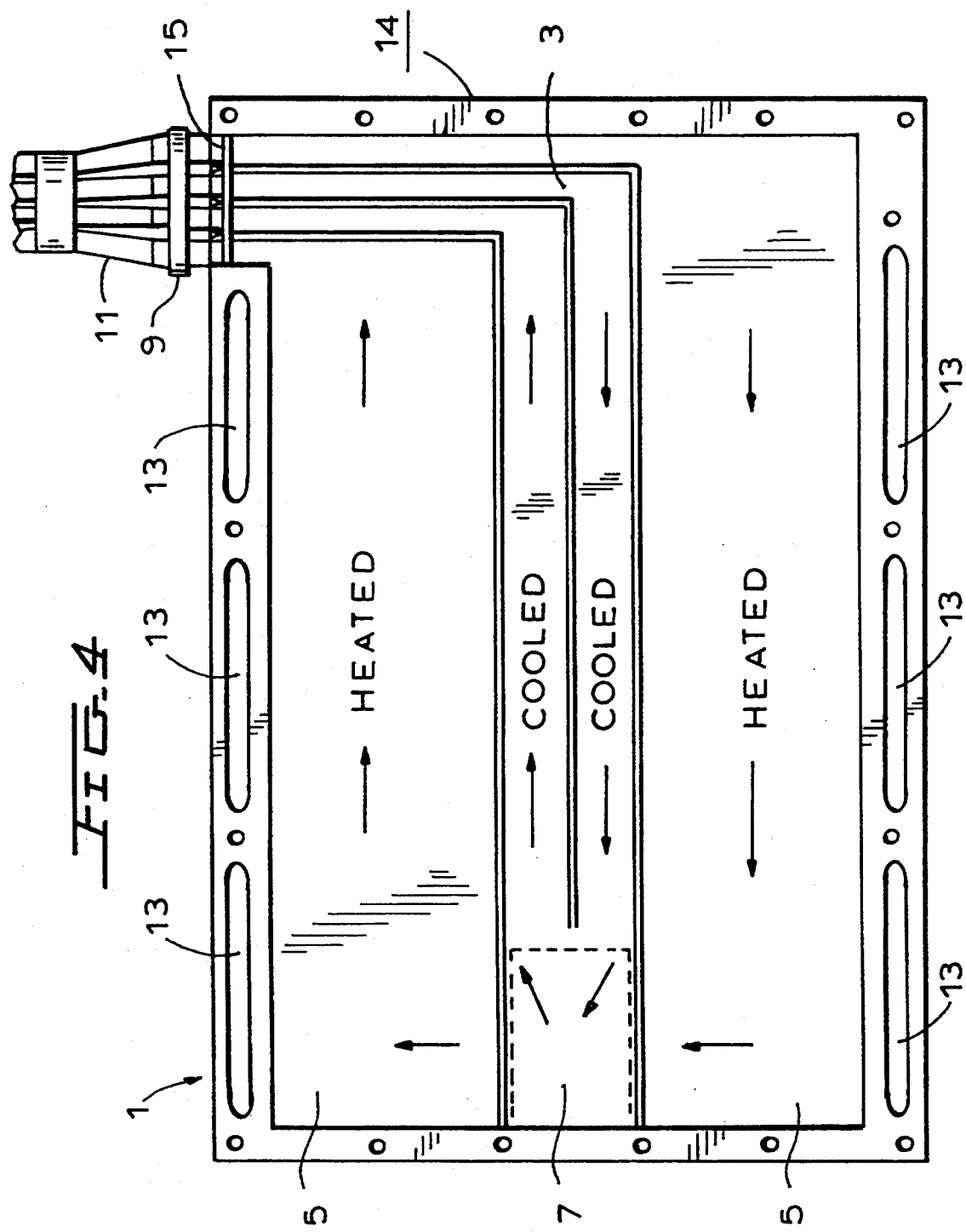

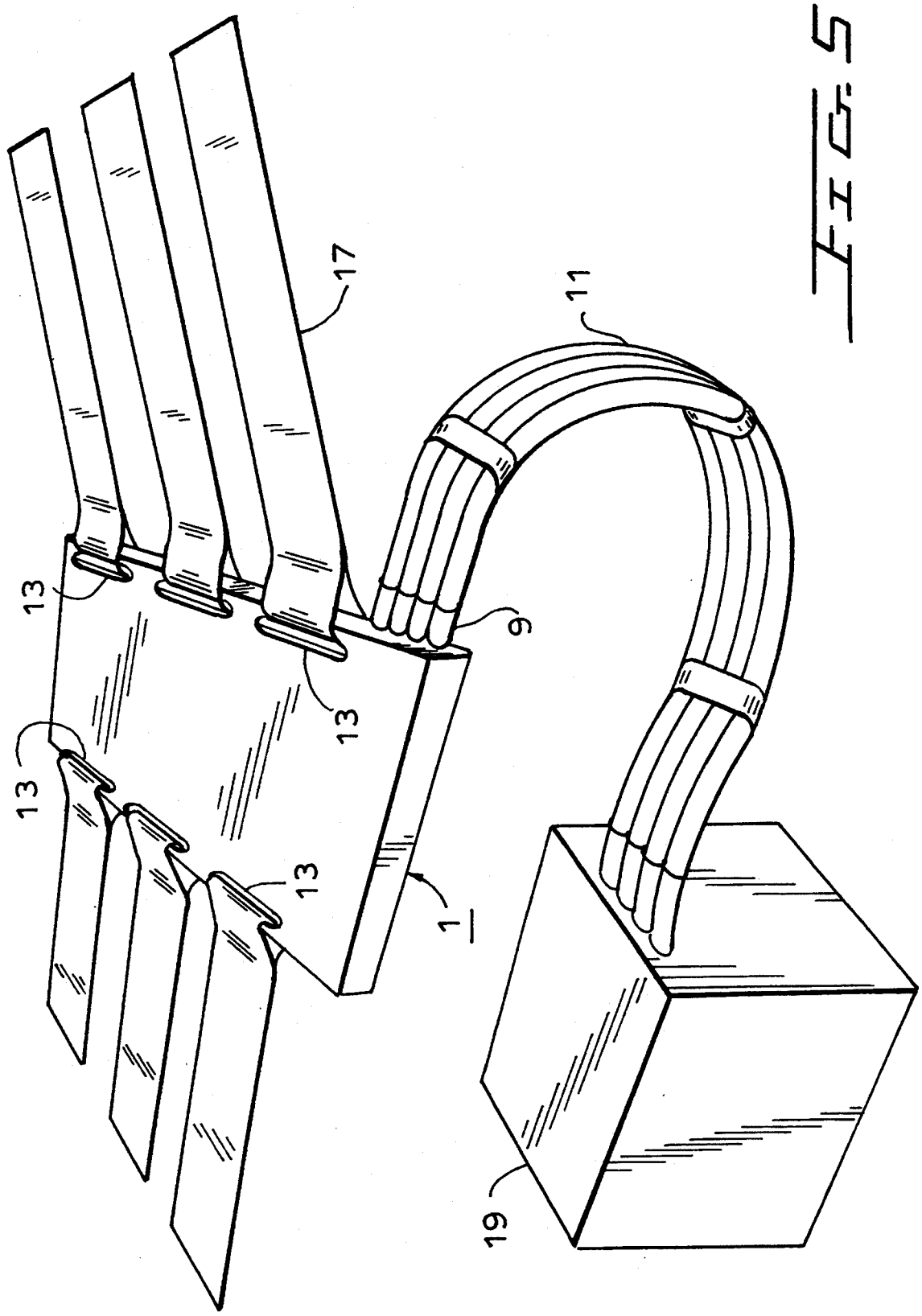

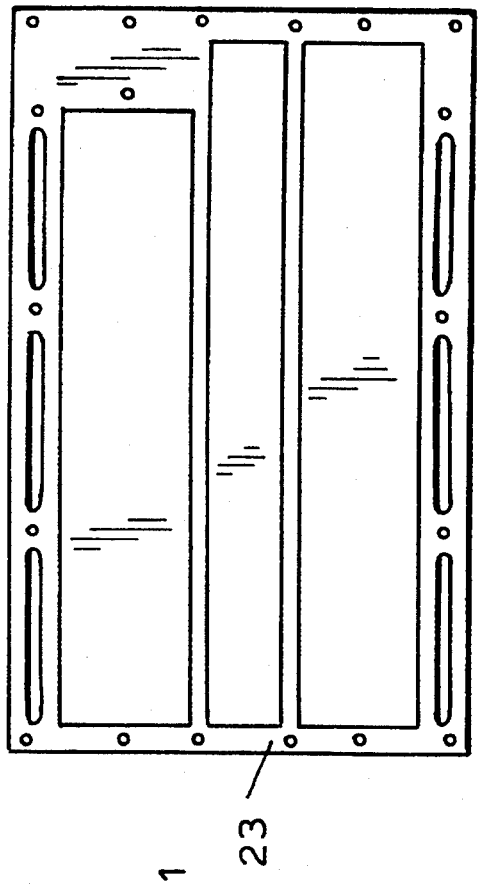
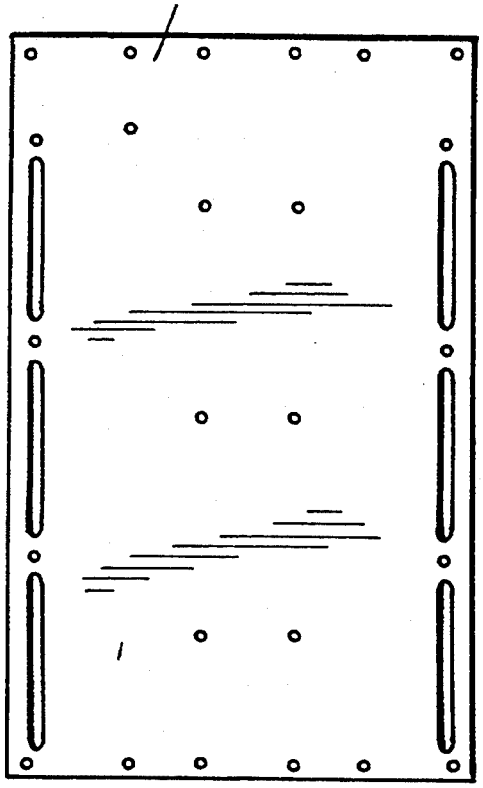
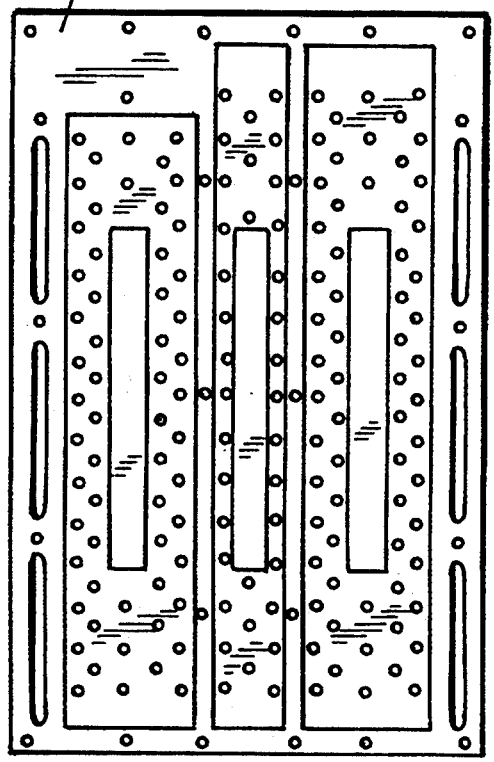

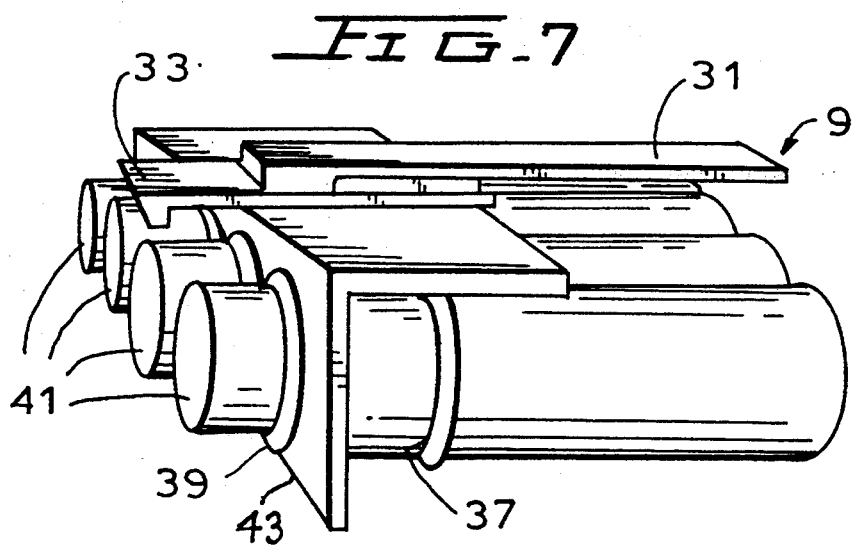
FIG_7
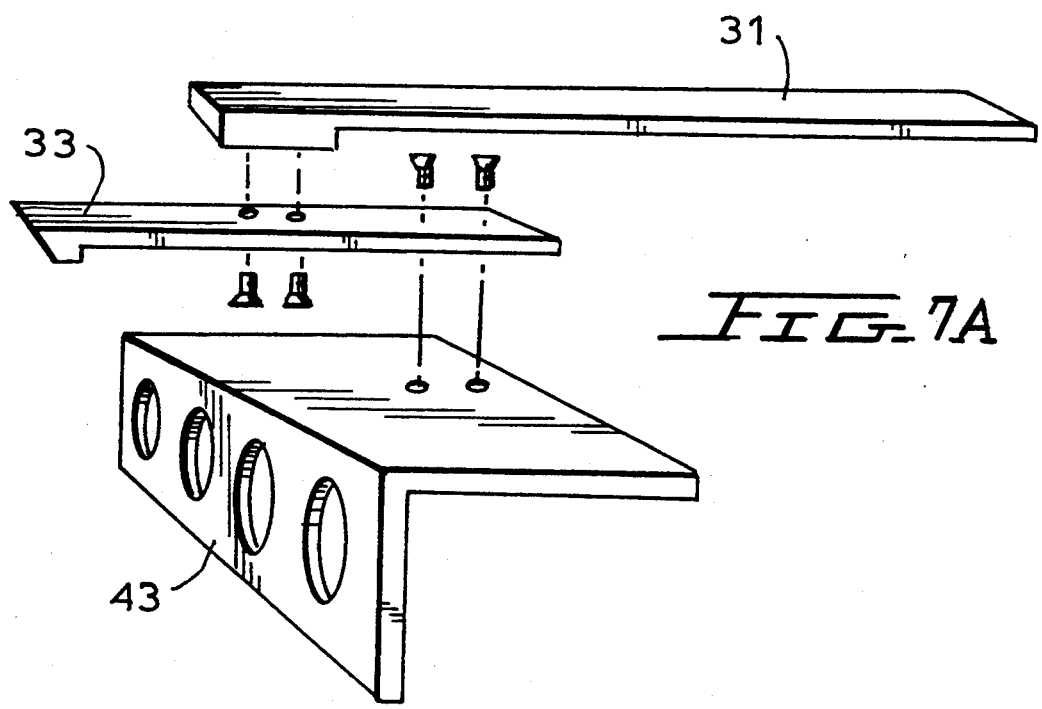
FIG_7A
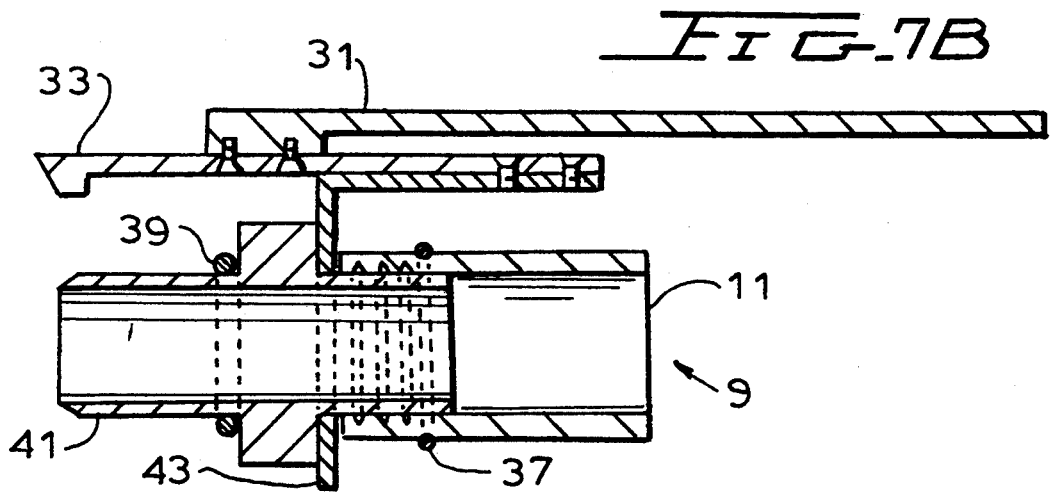
FIG_7B

THERMALLY-INTERACTIVE BACKBOARD

BACKGROUND OF THE INVENTION

1. Field of the Invention

The present invention relates to post-traumatic treatment of injuries, especially back and spinal injuries and, more specifically, to a thermally-interactive backboard with internal ducts for circulation of heated and/or cooled liquid or gas for treating a patient with a severe back injury.

2. Description of the Related Art

Trauma-related paralysis victims are often not paralyzed directly from their injuries, but rather from the inflammation and edema which frequently result from injury.

Unabated, or inadequately-abated, inflammation can result in soft tissue damage, including neurological damage (a primary contributor to paralysis), due to the manifestations of the physiological changes that occur during the inflammation or edema process. These hemodynamic changes include increased capillary permeability and leukocytic exudation.

The application of cold to the injury site helps to decrease the effects of inflammation and edema, and may prevent their advancement to an acute state. In cases of spinal injury, emergency medical service units often fail adequately to address both post-traumatic inflammation and edema, because immobilization and stabilization of the patient are their primary concerns.

SUMMARY OF THE INVENTION

Accordingly, it is an object of the present invention to provide a backboard which not only immobilizes and supports a post-trauma patient, but also cools the spinal area of the patient. In addition, hypothermia in the patient may be prevented by providing warmth to the rest of the patient's body and extremities.

Basically, the backboard of the present invention consists of a main body for supporting the patient, and a central duct within the main body of the backboard for circulating coolant along a central portion of the backboard adjacent the patient's spinal area. The main body of the backboard is also preferably provided with outer ducts for circulating heat along an outer portion of the backboard.

The backboard of the invention further includes quick-release connectors for coupling the central duct and/or the outer ducts to an external thermal unit containing a supply of cooling and/or heating fluids.

Preferably, an inflatable bladder is disposed between the main body of the backboard and the patient, the bladder being inflated to provide a surface which conforms to the contour of the patient. A perforated section is disposed between the main body of the backboard and the inflatable bladder, the perforated section providing both firm support to the patient's back and passages for the circulating coolant. A shroud is disposed between the bladder and the patient, the shroud providing a protective mask for the bladder, and securing the bladder to the perforated section.

With the above-noted structure, the backboard of the present invention advantageously provides a means by which post-traumatic inflammation and edema can be addressed from the onset by field personnel, Emergency Medical Services (EMS) units, etc., thereby preventing acute inflammation and/or edema. This makes it possible to provide substantially better control and prognosis.

Although the present invention may result in only a small reduction in paralysis in certain circumstances, where paralysis is concerned, any reduction can be of extreme importance.

Other features and advantages of the present invention will become apparent from the following description of the invention which refers to the accompanying drawings.

BRIEF DESCRIPTION OF THE DRAWINGS

FIG. 1 is a perspective view of the main body section of the backboard of the present invention, showing the recessed ducts, the crossover unit shape and location, the strap attachment and lifting points, and the inlet and outlet ports;

FIG. 1A is a perpective view of the crossover unit; and

FIGS. 1B and 1C are perspective and cross-sectional views, respectively, of the locking well for the quick-release mechanism of the present invention.

FIG. 2 is a cross section exploded cut-away view of the backboard of the present invention, detailing the ducts, threaded screw holes, screws and the relationship of the main body of the backboard, the shroud, the conforming bladder and the perforated section.

FIG. 3 is a cross section of an assembled backboard unit of the present invention with a patient, showing how the conforming bladder will, upon inflation, provide continual surface contact with the patient and eliminate any cavities which would reduce effectiveness.

FIG. 4 is a flow diagram of the ducts, indicating flow direction and duct type (cooled versus heated).

FIG. 5 is a perspective view of an assembled backboard unit connected to a thermal supply unit via feed lines to the backboard ports.

FIGS. 6, 6A, 6B, and 6C show further details of the components and relationships of a preferred embodiment of the present invention.

FIGS. 7, 7A, and 7B show perspective, perspective exploded, and cross-sectional views, respectively, of the connectors used to connect the feeder hoses to the main body for heating and cooling.

DETAILED DESCRIPTION OF THE PREFERRED EMBODIMENT

Referring first to FIG. 4, a preferred embodiment of the thermally-interactive anti-inflammatory backboard 1 is illustrated. Central duct 3 is shown conducting cooling fluid along the medial, spinal-supporting section of the device. Outer ducts 5 are shown conducting a heated fluid (liquid or gas) along the edges of the backboard supporting the outer torso and extremities of the patient. As described below, a cross-over section 7 provides flow of the heated fluid under the path of the central coolant duct 3, while avoiding interaction between the coolant and the heated fluid.

The central and outer ducts are provided with quick-release connectors 9 which allow for rapid attachment to feeder hoses 11 through which the appropriate fluids from an external thermal supply unit 19 (FIG. 5) are supplied. Strap-attaching/lifting points 13 are located along the edges of the backboard for connection of restraining belts, or for lifting of the board by emergency medical personnel, and the like.

In the preferred embodiment of the invention, the main body 14 of backboard 1 is molded from a polyethylene board having dimensions of ¾ thick, 16" wide and 32" long. Body 14 can also be made from polyethylene sheet stock, for example, with the recessed ducts machined out with a router or milling machine.

The inlet and outlet ports 15 (FIGS. 1 and 4) are smooth bore ½" ID and made with a drill press. The ports are connected to external thermal supply unit 19 via feeder hoses 11. Preferably, the connectors 41 for these hoses are smooth ½" O.D. nylon with rubber "O" rings 39. The four connectors are held together by a bracket 43 and lock onto the main body by a locking clip 33 (FIG. 7). Hoses 11 are secured on connectors 41 by rings 37 (FIG. 7). Also indicated in FIG. 5 are the locations for up to six restraint straps 17 (e.g., FERNO Model 430 straps).

Referring now to FIGS. 6, 6A, 6B and 6C, various components of a preferred embodiment of the invention are detailed. An inflatable bladder 21 is provided between the main body 14 and the patient, the bladder being inflated to provide a surface which conforms to the contour of the patient. The bladder is preferably made from 1/32" thick soft rubber and is inflated from below, as shown in FIG. 3.

A perforated section 25 is located under the bladder 21. Perforated section 25 provides firm support to the patient's back, while at the same time provides passages for the heated and cooled mediums via holes ⅛" in diameter distributed in the two heated areas and the centrally cooling area of the backboard. The perforated section 25 is preferably made from polyethylene sheet stock of ¼" thickness.

A shroud 23 is provided over bladder 21. The function of shroud 23 is to mask the bladder 21 and to maintain a separation between heated and cooled areas and to secure the bladder 21 firmly in place against perforated section 25. Shroud 23 is preferably made from 1/16" thick nylon sheet stock.

As shown in FIGS. 1 and 1A, cross-over unit 7 is cemented to the floor of main body 14 to provide a duct for the passage of heat from the right side of the main body to the left under the cooled ducts. Cross-over 7 is molded from polyethylene.

The backboard of the invention is advantageously designed with quick-release connectors 9 such that all feeder lines can be simultaneously attached and detached from the main body 14 without the need for tools. Referring to the detail of quick-release connector 9 shown in FIGS. 7, 7A and 7B, locking clip 33 will drop into a locking well 35 (FIGS. 1B and 1C) upon insertion of the hoses/quick connector assembly and secure a hoses until the release lever 31 is depressed, facilitating simultaneous release of all four hoses.

The invention may be used in conjunction with, or prior to, an invasive type of device to be employed at a hospital should the severity of an injury warrant more extreme measures to abate inflammation, such as subsurface, localized cooling via thermal probes.

Advantageously, the thermally-interactive backboard of the present invention is designed such that it need not be connected to the thermal supply unit's thermal feed lines (FIG. 5) until it is convenient. Thus, the backboard of the invention can be used by EMS personnel in the same manner as current passive units. EMS personnel will not be constrained by any impediment, such as the feeder hoses, during a difficult deployment of the device, e.g., placing the backboard in place and strapping the patient to it, while the patient is seated in a wrecked vehicle or aircraft. Upon extraction of the patient from such an accident, the backboard of the invention can then be connected to the thermal supply unit. The patient can be placed on a medical cot without removing the backboard, which preferably will be 16"W×32"L, and therefore compatible with standard cots such as the three-level roll-in cot (FERNO Model 29-M).

Heating of the unit's outer ducts (FIGS. 1, 3 and 4) is employed to prevent hypothermia of the patient, which may be induced, for example, by either the injury-related trauma, or from the cooling of the spinal area by the backboard. This heating can be performed simultaneously with the cooling, as the heating and cooling function independently of each other. In cases where back injury is not of concern, the heating feature of the backboard can used without the use of cooling, and the central ducts themselves could be used for heating, both to prevent hypothermia and to treat post-traumatic shock.

For maximum effect, the patient should not be removed from the interactive backboard until the threat of inflammation or edema is no longer evident, which may take approximately 72 hours. Radiolucent materials are extensively used throughout the backboard, enabling diagnosis, and thus, continual use. Materials compatible with sterilization procedures are also preferably employed in the construction of the backboard.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

What is claimed is:

1. A backboard for cooling a patient's spinal area, the backboard comprising:
    a main body for supporting the patient;
    a central duct within the main body of the backboard for circulating a coolant along a portion of the backboard adjacent the patient's spinal area;
    at least one outer duct within the main body of the backboard for circulating a heated fluid along an outer portion of the backboard; and
    means for simultaneously delivering the coolant to the central duct and the heated fluid to the outer duct.

2. The backboard of claim 1, further comprising cross-over means within the main body of the backboard for allowing said coolant to pass by said heated fluid without interaction therebetween.

3. The backboard of claim 1, further comprising an inflatable bladder disposed on the main body and adapted to lie between the main body of the backboard and the patient, said bladder being inflated to provide a surface which conforms to the contour of the patient.

4. The backboard of claim 3, further comprising a perforated section disposed between the main body of the backboard and the inflatable bladder, said perforated section providing both firm support to the patient's back and passages for the circulating coolant.

5. The backboard of claim 4, further comprising a shroud disposed over the bladder and adapted to lie between the bladder and the patient, said shroud providing a protective mask for the bladder, and securing the bladder to the perforated section.

* * * * *